US00PP35859P2

(12) United States Plant Patent
Scheiber et al.

(10) Patent No.: US PP35,859 P2
(45) Date of Patent: Jun. 4, 2024

(54) ***SALVIA* PLANT NAMED 'BALSALSLENT'**

(50) Latin Name: *Salvia officinalis*
Varietal Denomination: Balsalslent

(71) Applicant: Ball Horticultural Company, West Chicago, IL (US)

(72) Inventors: Sloane Michele Scheiber, Parkesburg, PA (US); Emily E. Alff, Royersford, PA (US)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 18/371,961

(22) Filed: Sep. 22, 2023

(51) Int. Cl.
*A01H 5/02* (2018.01)
*A01H 6/50* (2018.01)

(52) U.S. Cl.
USPC ..... Plt./475
CPC ..... *A01H 6/508* (2018.05)

(58) Field of Classification Search
USPC ..... Plt./475
CPC ..... A01H 6/508; A01H 5/02
See application file for complete search history.

*Primary Examiner* — Keith O. Robinson
(74) *Attorney, Agent, or Firm* — Audrey Charles

(57) ABSTRACT

A new and distinct cultivar of *Salvia* plant named 'Balsalslent', characterized by its medium violet-blue colored flowers, medium grey-green foliage, and moderately vigorous, compact-mounded growth habit, is disclosed.

1 Drawing Sheet

Latin name of genus and species of plant claimed: *Salvia officinalis*.

Variety denomination: 'Balsalslent'.

BACKGROUND OF THE INVENTION

The present invention relates to a new and distinct cultivar of *Salvia* plant botanically known as *Salvia officinalis* and hereinafter referred to by the cultivar name 'Balsalslent'.

The new cultivar originated in a controlled breeding program in Cochranville, Pennsylvania. The objective of the breeding program was the development of *Salvia* cultivars having numerous inflorescences while maintaining culinary appeal.

The new *Salvia officinalis* cultivar is a chemical-induced sport of *Salvia officinalis*, common sage, not patented, characterized by its medium violet-blue colored flowers, light grey-green colored foliage, and moderately vigorous, semi-upright growth habit. The chemical mutation treatment occurred during November 2016. The new cultivar was discovered as a side shoot and selected during May 2019 in a controlled environment in Cochranville, Pennsylvania.

Asexual reproduction of the new cultivar by terminal stem cuttings since May 2019 in Cochranville, Pennsylvania and Elburn, Illinois has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Balsalslent' as a new and distinct cultivar of *Salvia* plant:

1. Medium violet-blue colored flowers;
2. Medium grey-green foliage; and
3. Moderately vigorous, compact-mounded growth habit.

Plants of the new cultivar differ from plants of the parent primarily in having more inflorescences per plant, and darker green colored calyx, a more compact-mounded growth habit, and more branches per plant.

Of the many commercially available *Salvia* cultivars, the most similar in comparison to the new cultivar is 'Berggarten', not patented. However, in side-by-side comparisons, plants of the new cultivar differ from plants of 'Berggarten' in at least the following characteristics:

1. Plants of the new cultivar have more inflorescences per plant than plants of 'Berggarten'; and
2. Plants of the new cultivar have narrower leaves than plants of 'Berggarten'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balsalslent'. The plants were approximately 14-months old. The plants were given one pinch one week before transplant into five-gallon containers. Plants were grown in an outdoor nursery in West Chicago, Illinois for approximately four months and then overwintered in a polycarbonate greenhouse in Elburn, Illinois.

DETAILED BOTANICAL DESCRIPTION

Figure 1:
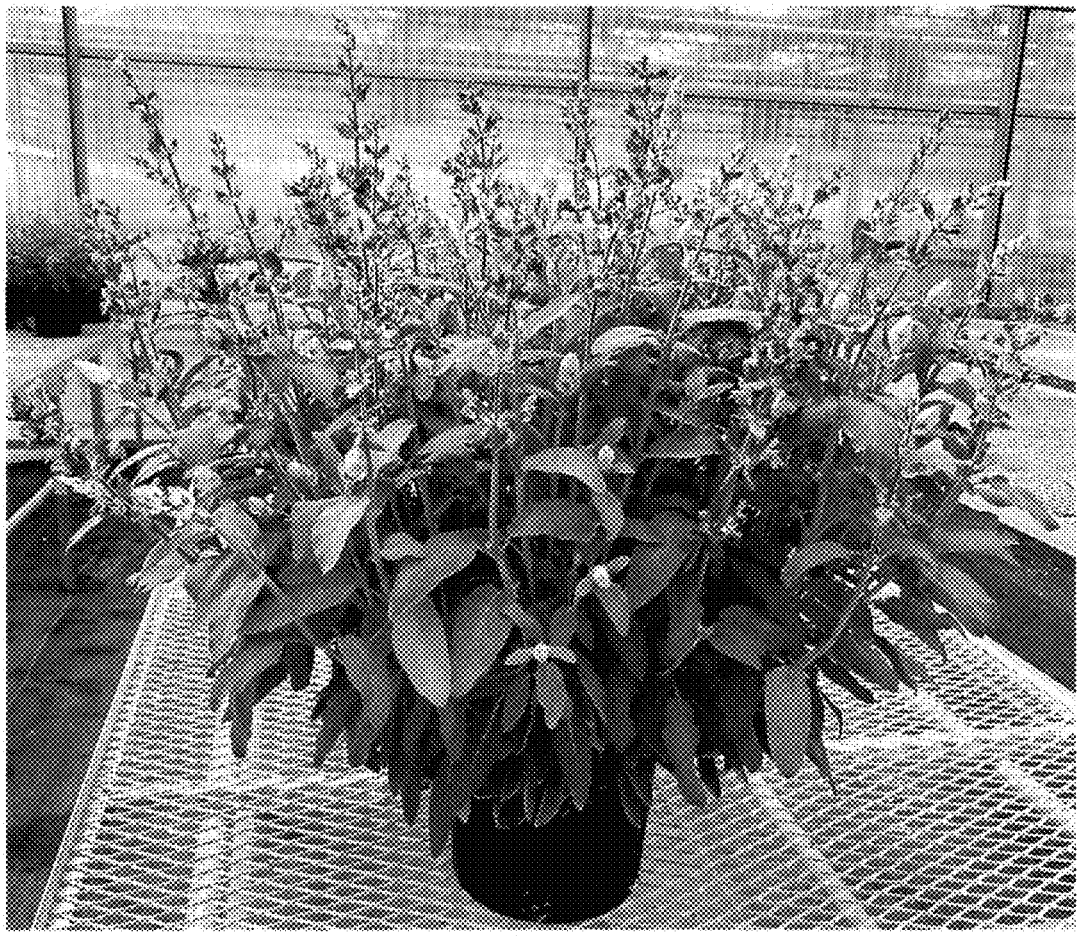
FIG. 1 illustrates a side view of the overall growth and flowering habit of 'Balsalslent'.
Figure 2:
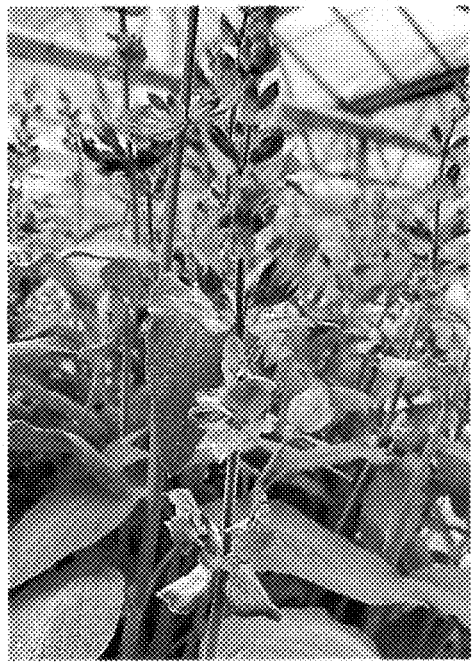
FIG. 2 illustrates a close-up view of an inflorescence of 'Balsalslent'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in May 2023 under natural light conditions in Naperville, Illinois.

The following descriptions and measurements describe approximately 14-month-old plants produced from cuttings from stock plants and grown under conditions comparable to those used in commercial practice. The plants were grown in five-gallon containers in an outdoor nursery in West Chicago, Illinois for approximately four months and then overwintered in a polycarbonate greenhouse in Elburn, Illinois. Overwintering greenhouse temperatures were maintained at approximately 60° F. to 65° F. (15.5° C. to 18.3° C.) during the day and approximately 55° F. to 60° F. (12.7° C. to 15.5° C.) during the night. No supplemental lighting was provided during overwintering. Measurements and numerical values represent averages of typical plants.

Botanical classification: *Salvia officinalis* 'Balsalslent'.

Parentage:

*Parent.*—*Salvia officinalis*, common sage, not patented.

Propagation:

*Type cutting.*—Terminal stem.

*Time to initiate roots.*—Approximately 5 to 7 days.

*Time to produce a rooted cutting.*—Approximately 35 to 42 days.

*Root description.*—Fine, fibrous.

*Rooting habit.*—Freely branching.

Plant description:

*Commercial crop time.*—Approximately 10 to 12 weeks from a rooted cutting to finish in a 15 cm container.

*Growth habit and general appearance.*—Herbaceous perennial, moderately vigorous, compact-mounded growth habit.

*Hardiness.*—USDA Zone 5a (−20° F. to −15° F./−28.9° C. to −26° C.).

*Size.*—Height from soil level to top of plant plane: Approximately 58.0 cm. Width: Approximately 90.0 cm.

*Branching habit.*—Freely branching. Pinching enhances lateral branching. Quantity of branches per plant: Approximately 7.

*Branch.*—Shape: Square in cross section. Strength: Strong. Length to base of inflorescence: Approximately 33.0 cm. Diameter: Approximately 5.0 mm to 7.0 mm. Length of central internode: Approximately 7.5 cm. Texture: Tomentose. Pubescence color: NN155A. Color of young and mature stems: 146B, color appears lighter due to pubescence, stem bases become woody 200B with age.

Foliage description:

*General description.*—Quantity of leaves per main branch: Approximately 18, clustered at base. Fragrance: Strong, sage-like. Form: Simple. Arrangement: Opposite.

*Leaves.*—Aspect: Petiole acute angle to stem, leaf blade becomes obtuse angle with age. Shape: Ovate. Margin: Minutely crenate. Apex: Acute. Base: Obtuse. Venation pattern: Pinnate. Length of mature leaf: Approximately 8.5 cm. Width of mature leaf: Approximately 3.3 cm. Texture of upper and lower surfaces: Densely pubescent with a mixture of glandular and short, fine hairs, reticulate. Pubescence color: NN155D. Color of upper surface of young and mature foliage: 138A with slightly darker venation, pubescence color is more visible on younger leaves. Color of lower surface of young and mature foliage: Closest to 138B with venation of closest to 147D.

*Petiole.*—Length: Approximately 2.5 cm to 6.5 cm. Diameter: Approximately 2.0 mm. Tomentose. Pubescence color: NN155A. Color: 147D with 138B, color appears lighter due to pubescence.

Flowering description:

*Flowering habit.*—'Balsalslent' is a short-day obligate freely flowering under outdoor growing conditions with substantially continuous blooming from April through May.

*Lastingness of individual floret.*—Approximately 4 to 5 days.

Inflorescence description:

*General description.*—Type: Spikes in verticillaster arrangement, florets in clusters of approximately 5, not persistent, often slightly curved with age. Quantity of inflorescences per plant: Approximately 80. Fragrance: Moderately strong, sweet. Length or height of inflorescence: Approximately 8.0 cm to 14.0 cm. Width of inflorescence: Approximately 5.0 cm. Quantity of fully-open flowers per inflorescence: Approximately 7 to 14, one to two per cluster open at one time.

*Peduncle.*—Shape: Square in cross section. Strength: Strong. Aspect: Erect. Length: Approximately 4.0 cm to 7.0 cm. Diameter: Approximately 3.0 mm. Texture: Tomentose. Color of pubescence: NN155A. Color: 146B, color appears lighter due to pubescence.

Flower description:

*Type.*—Single, zygomorphic.

*Bud.*—Rate of opening: Generally takes 3 to 4 days for bud to progress from first color to fully open flower.

*Bud just before opening.*—Shape: Obovoid. Length: Approximately 1.5 cm. Diameter: Approximately 5.0 mm. Texture: Densely pubescent. Color: Calyx of 146B tinted with 187A and petal portion of 92A.

*Corolla.*—Shape: Bilabiate, lower lip having three lobes, base fused. Width: Approximately 1.1 cm. Length: Approximately 1.5 cm. Depth: Approximately 2.4 cm.

*Upper lip.*—Shape: Hooded. Margin: Entire. Apex: Rounded. Length from throat: Approximately 1.0 cm. Width: Approximately 4.0 mm. Texture of inner surface: Glabrous. Texture of outer surface: Moderately pubescent. Color of pubescence: 93D and NN155A. Color of inner surface when first and fully open: 92B. Color of outer surface when first and fully open: 93D.

*Lower lip.*—Shape of central lobe: Obovate. Shape of lateral lobes: Oblong with side edges strongly curved under petal. Margin: Entire. Apex of central lobe: Emarginate. Apex of lateral lobes: Apiculate. Length from throat of central lobe: Approximately 1.1 cm. Width of central lobe: Approximately 1.1 cm. Length from throat of lateral lobes: Approximately 7.0 mm. Width of lateral lobes: Approximately 4.0 mm. Texture of upper surface: Glabrous. Texture of lower surface: Moderately pubescent. Color of upper surface of central lobe when first and fully open: 93B with two nectar glides of NN155D. Color of lower surface of central lobe when first and fully open: 93C. Color of upper surface of lateral lobes when first and fully open: 92B. Color of lower surface of lateral lobes when first and fully open: 92C to 92D.

*Corolla tube*.—Length: Approximately 1.5 cm. Diameter at opening: Approximately 7.0 mm. Diameter at base: Approximately 3.0 mm. Texture of inner surface: Glabrous. Texture of outer surface: Moderately pubescent. Color of inner and outer surface when first and fully open: 93D with NN155D.

*Calyx*.—Shape: Tubular. Length: Approximately 1.5 cm. Diameter: Approximately 1.1 cm.

*Sepals*.—Quantity per flower: Fused into two lobes. Shape: Obovate. Apex: Upper lobe three acute tips, lower lobe notched. Length: Approximately 1.5 cm. Width of lobes: Approximately 9.0 mm. Texture of inner surface: Glabrous. Texture of outer surface: Tomentose. Color of pubescence: NN155C. Color of inner surface: 146C with 155C. Color of outer surface: 146B tinted with 187A.

*Bracts*.—Quantity: One bract located at the base of each floret cluster. Shape: Ovate, concave. Length: Approximately 1.6 cm. Width: Approximately 1.0 cm. Texture of inner surface: Sparsely pubescent. Texture of outer surface: Moderately pubescent. Color of upper surface: 138A to 138C sometimes tinted with 187A. Color of lower surface: 138B to 138D.

*Pedicel*.—Strength: Strong, flexible. Aspect: At an acute angle. Length: Approximately 2.0 mm. Diameter: Approximately 1.0 mm. Texture: Tomentose. Color of pubescence: NN155A. Color: 146B, color appears lighter due to pubescence.

*Reproductive organs*.—Androecium: Stamen quantity: 2 per flower, dorsifixed, strongly curved. Stamen length: Approximately 7.0 mm. Filament length: Approximately 5.0 mm. Filament color: NN155D lightly tinted with 93B. Anther shape: Irregular oblong. Anther length: Approximately 2.0 mm. Anther color: 160C. Pollen amount: Not observed. Gynoecium: Pistil quantity: 1 per flower, slightly curved. Pistil length: Approximately 2.4 cm. Stigma shape: Cleft, two-parted. Stigma length: 2.0 mm. Stigma color: 93B. Style length: Approximately 2.0 cm. Style color: NN155D lightly tinted with 93B, opaque. Style texture: Glabrous. Ovary length: Approximately 2.0 mm. Ovary color: 144A and 93A.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Balsalslent', substantially as herein illustrated and described.

* * * * *